United States Patent
Lee et al.

(10) Patent No.: US 11,246,553 B2
(45) Date of Patent: Feb. 15, 2022

(54) RADIOGRAPHIC APPARATUS AND RADIOGRAPHIC METHOD USING SAME

(71) Applicant: DRTECH CORP, Seongnam-Si (KR)

(72) Inventors: Sang Il Lee, Yongin-Si (KR); Eung Bum Kim, Hwaseong-Si (KR); Choul Woo Shin, Seongnam-Si (KR)

(73) Assignee: DRTECH CORP

( * ) Notice: Subject to any disclaimer, the term of this patent is extended or adjusted under 35 U.S.C. 154(b) by 0 days.

(21) Appl. No.: 16/466,289

(22) PCT Filed: Dec. 1, 2017

(86) PCT No.: PCT/KR2017/014035
§ 371 (c)(1),
(2) Date: Jun. 3, 2019

(87) PCT Pub. No.: WO2018/105963
PCT Pub. Date: Jun. 14, 2018

(65) Prior Publication Data
US 2019/0388050 A1    Dec. 26, 2019

(30) Foreign Application Priority Data

Dec. 7, 2016 (KR) .......... 10-2016-0166020

(51) Int. Cl.
*A61B 6/00* (2006.01)

(52) U.S. Cl.
CPC .............. *A61B 6/54* (2013.01); *A61B 6/4007* (2013.01); *A61B 6/4028* (2013.01)

(58) Field of Classification Search
CPC ......... A61B 6/00; A61B 6/025; A61B 6/4007; A61B 6/4028; A61B 6/502; A61B 6/54; A61B 6/542
See application file for complete search history.

(56) References Cited

U.S. PATENT DOCUMENTS 4,349,740 A * 9/1982 Grassmann .......... A61B 6/4028
378/25
4,383,733 A * 5/1983 Weiss ...................... G03H 1/06
359/210.1
(Continued)

FOREIGN PATENT DOCUMENTS

DE   102010011663 A1   9/2011
JP      2008104673 A    5/2008
(Continued)

OTHER PUBLICATIONS

Written Opinion for PCT/KR2017/014035 dated Feb. 7, 2018.
(Continued)

*Primary Examiner* — Dani Fox
*Assistant Examiner* — Soorena Kefayati
(74) *Attorney, Agent, or Firm* — Renaissance IP Law Group LLP (57) ABSTRACT

A radiographic apparatus generates images of objects of interest, such as subject body parts, using radiation. The radiographic apparatus includes a radiation irradiating unit having a plurality of radiation sources, where each of the plurality of radiation sources irradiates the object of interest, a driving unit for moving the radiation irradiating unit, and a radiation detector for detecting the radiation passing through the objects of interest from each of the plurality of radiation sources.

16 Claims, 6 Drawing Sheets

(56) References Cited

U.S. PATENT DOCUMENTS

| | | | | |
|---|---|---|---|---|
| 4,513,433 | A * | 4/1985 | Weiss | G01N 23/044 378/2 |
| 8,189,893 | B2 * | 5/2012 | Zhang | G01N 23/00 382/131 |
| 8,699,661 | B2 * | 4/2014 | Jang | A61B 6/5235 378/37 |
| 9,322,931 | B2 * | 4/2016 | Ohta | A61B 6/025 |
| 10,806,420 | B2 * | 10/2020 | Mohammadi | H01J 35/065 |
| 2006/0039529 | A1 * | 2/2006 | Tsubaki | A61B 6/022 378/41 |
| 2009/0022264 | A1 * | 1/2009 | Zhou | A61B 6/025 378/5 |
| 2009/0232272 | A1 * | 9/2009 | Tsujii | A61B 6/00 378/16 |
| 2009/0323893 | A1 * | 12/2009 | Hanke | A61B 6/025 378/37 |
| 2010/0091940 | A1 * | 4/2010 | Ludwig | A61B 6/502 378/22 |
| 2010/0329416 | A1 * | 12/2010 | Tsujii | A61B 6/589 378/21 |
| 2011/0002441 | A1 * | 1/2011 | Vogtmeier | A61B 6/4007 378/21 |
| 2011/0206177 | A1 * | 8/2011 | Hirasawa | A61B 6/542 378/16 |
| 2012/0008739 | A1 * | 1/2012 | Hoernig | A61B 6/502 378/37 |
| 2012/0014512 | A1 * | 1/2012 | Kim | A61B 6/54 378/189 |
| 2012/0051510 | A1 * | 3/2012 | Ohta | A61B 6/542 378/62 |
| 2012/0057672 | A1 * | 3/2012 | Jang | A61B 6/502 378/37 |
| 2012/0076260 | A1 * | 3/2012 | Kitagawa | A61B 6/022 378/41 |
| 2012/0076265 | A1 * | 3/2012 | Ohta | A61B 6/4283 378/62 |
| 2012/0195403 | A1 * | 8/2012 | Vedantham | A61B 6/5282 378/4 |
| 2014/0010345 | A1 * | 1/2014 | Ishiyama | H05G 1/70 378/41 |
| 2014/0112434 | A1 * | 4/2014 | Jang | A61B 6/502 378/37 |
| 2014/0209806 | A1 * | 7/2014 | Nishino | A61B 6/4007 250/363.01 |
| 2015/0030119 | A1 * | 1/2015 | Tamura | A61B 6/4007 378/9 |
| 2016/0262710 | A1 * | 9/2016 | Baek | A61B 6/4007 |
| 2021/0165113 | A1 * | 6/2021 | Nukanobu | G01T 1/175 |

FOREIGN PATENT DOCUMENTS

| | | |
|---|---|---|
| JP | 2010233962 A | 10/2010 |
| JP | 2011125698 A | 6/2011 |
| KR | 20060002871 A | 1/2006 |
| KR | 20120006698 A | 1/2012 |
| KR | 20140050479 A | 4/2014 |
| KR | 20140087206 A | 7/2014 |
| KR | 20150052596 A | 5/2015 |
| KR | 20160026145 A | 3/2016 |
| KR | 20160118637 A | 10/2016 |

OTHER PUBLICATIONS

International Search Report for PCT/KR2017/014035 dated Feb. 7, 2018.

Extended European Search Report for Application No. 17879426.9 dated May 27, 2020.

* cited by examiner

FIG. 1

Prior Art

FIG. 2

Prior Art

RADIOGRAPHIC APPARATUS AND RADIOGRAPHIC METHOD USING SAME

TECHNICAL FIELD

The present disclosure relates to a radiographic apparatus and a radiographic method using the same, and more particularly, to a radiographic apparatus for capturing an image of an object by using radiation and a radiographic method using the same.

BACKGROUND ART

Recently, radiography technology has rapidly evolved into digital imaging technology that has a variety of advantages such as a relatively high resolution, a wide dynamic range, a simple generation of an electrical signal, and easy data processing and storage instead of a conventional analog method using a film, while being incorporated into semiconductor technology. Digital imaging technology meets the clinical and environmental requirements of an early diagnosis of a disease based on improved diagnostic ability of a digital image.

Therefore, digital mammography technology has been proposed which is a breast dedicated radiography technology capable of detecting a lesion and a micro-calcification for detection and early diagnosis of a breast cancer by expressing the internal structure of the breast, which is an object for radiography, as a high resolution image by utilizing the unique biological tissue contrast ability of radiation. The digital mammography technology has rapidly propagated owing to having unique characteristics such as image expansion, a reduction in the number of times of photography, an increase in resolution, and minimization of exposure through adjustment of brightness and contrast ratio, together with various advantages of the digital imaging technology.

Meanwhile, a radiographic apparatus for obtaining a two-dimensional projection image has difficulty in diagnosing an abnormal area (lesion) of an object when the abnormal area is covered by human tissues or the like. As a solution of the problem, a technique for generating a three-dimensional image for a subject by photographing an object at various angles and then synthesizing the images has been developed.

To this end, a radiographic apparatus used in the conventional digital breast tomosynthesis (DBT) system generates multidirectional radiation projection images by irradiating an object with radiation while rotating one radiation source relatively with respect to the object and synthesizes the images to generate a three-dimensional image.

The conventional radiographic apparatus lowers image quality because movement of a radiation source causes a motion blur phenomenon that the boundary of an image acquired by a radiation detector appears unclear. A stop and shoot method can also be used for stopping a radiation source completely at a desired photographing angle in order to prevent such a motion blur phenomenon and capturing the projection image and then moving the radiation source to a next position and capturing the image. However, the method has a problem that the total photographing time is increased because the photographing is performed while the radiation source comes to a complete stop.

PRIOR ART DOCUMENT

Japanese Patent Publication No. 2011-125698

DISCLOSURE

Technical Problem

The present disclosure provides a radiographic apparatus capable of acquiring a plurality of radiation images in various directions and a radiographic method using the same.

Technical Solution

In accordance with an exemplary embodiment, a radiographic apparatus includes: a radiation irradiating unit having a plurality of radiation sources and configured to irradiate an object with radiation emitted from each of the plurality of radiation sources; a driving unit configured to move the radiation irradiating unit; and a radiation detector configured to detect the radiation passing through the object to acquire a plurality of radiation images.

The radiation sources may be arranged in one direction, and the radiation irradiating unit may move in a direction in which the radiation sources are arranged.

The radiation sources may move integrally with the radiation irradiating unit with an interval maintained therebetween.

The radiation sources may be provided on the radiation irradiating unit at the same intervals.

The driving unit may move the radiation irradiating unit such that the radiation sources are arranged at positions at which the radiation sources do not overlap each other before and after the movement of the radiation irradiating unit.

The driving unit may move the radiation irradiating unit by a distance shorter than an interval between the radiation sources.

The radiographic apparatus may further include a controller configured to control a direction of irradiation of each radiation source according to the movement of the radiation irradiating unit.

The controller may control the direction of irradiation of each radiation source such that the direction of irradiation faces the same position as that before and after the movement of the radiation irradiating unit.

An amount of emission of radiation from the radiation source may be controlled according to a distance between the radiation source and the radiation detector in a direction of irradiation of the radiation source.

The radiation source may include a field emission electrode configured to generate electrons by applying an electric field.

The radiation source may include a thermionic emission electrode configured to generate electrons by heating a filament.

In accordance with another exemplary embodiment, a radiographic method includes: acquiring a plurality of first radiation images by irradiating an object with radiation emitted from a radiation irradiating unit having a plurality of radiation sources; moving the radiation irradiating unit in a direction in which the radiation sources are arranged; and acquiring a plurality of second radiation images by irradiating the object with radiation emitted from the radiation irradiating unit.

The acquiring of the first radiation images and the acquiring of the second radiation images may include respectively acquiring the plurality of first radiation images and the plurality of second radiation images by sequentially activating the respective radiation sources.

The acquiring of the first radiation images and the acquiring of the second radiation images may include respectively acquiring the plurality of first radiation images and the plurality of second radiation images by activating the respective radiation sources in random order.

The acquiring of the first radiation images and the acquiring of the second radiation images may include respectively acquiring the plurality of first radiation images and the plurality of second radiation images by allowing radiation emitted from at least two of the radiation sources to be incident on the object at different intensities.

The acquiring of the first radiation images and the acquiring of the second radiation images may include respectively acquiring the plurality of first radiation images and the plurality of second radiation images by adjusting an amount of emission of radiation emitted from each of the radiation sources such that the radiation is incident on the object at a uniform intensity.

The radiographic method may further include changing a direction of irradiation of each of the radiation sources such that the direction of irradiation faces the same position as that before the moving of the radiation irradiating unit.

The changing of the direction of irradiation of the radiation source may be performed simultaneously with the moving of the radiation irradiating unit.

Advantageous Effects

The radiographic apparatus and the radiographic method using the same, in accordance with embodiments of the present disclosure, may reduce the number of radiation sources by synthesizing a three-dimensional image by using a plurality of first radiation projection images and a plurality of second radiation projection images captured at respective positions through movement of a radiation irradiating unit on which a plurality of radiation sources are provided. Thus, an installation space may be obtained, product costs may be reduced, and maintenance and repair may be easily performed.

In addition, a motion blur phenomenon due to movement of the radiation sources may be prevented by capturing an image in a state in which a number of radiation sources less than the number of radiation projection images required to synthesize the three-dimensional image are fixed, and a photographing time for acquisition of an entire radiation projection image may be reduced by minimizing a moving distance of the radiation irradiating unit.

Furthermore, the radiographic apparatus and the radiographic method using the same, in accordance with embodiments of the present disclosure, may quickly capture the radiation projection images of an object at various angles through the plurality of radiation sources arranged in a predetermined direction so as to acquire a high-resolution three-dimensional image, thereby enabling an accurate diagnosis of a lesion for the object.

DETAILED DESCRIPTION

Hereinafter, embodiments of the present disclosure will be described in detail with reference to the accompanying drawings. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. Like reference numerals refer to like elements throughout.

Figure 1:
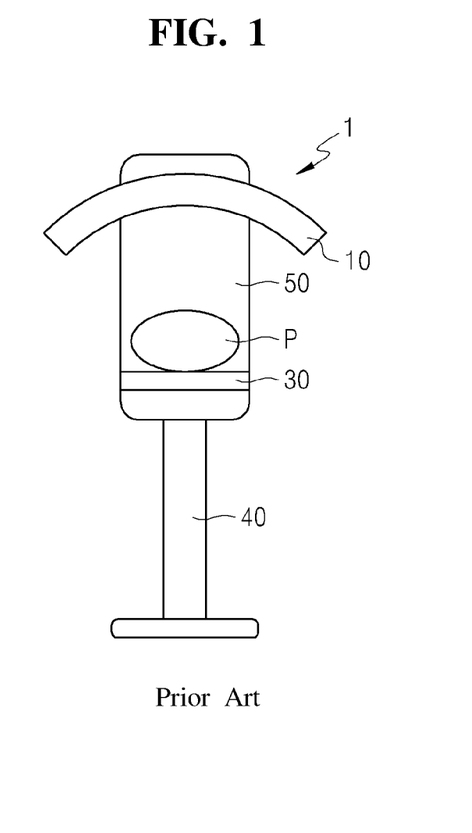
FIG. 1 is a view illustrating a digital breast tomosynthesis (DBT) device.
Figure 2:
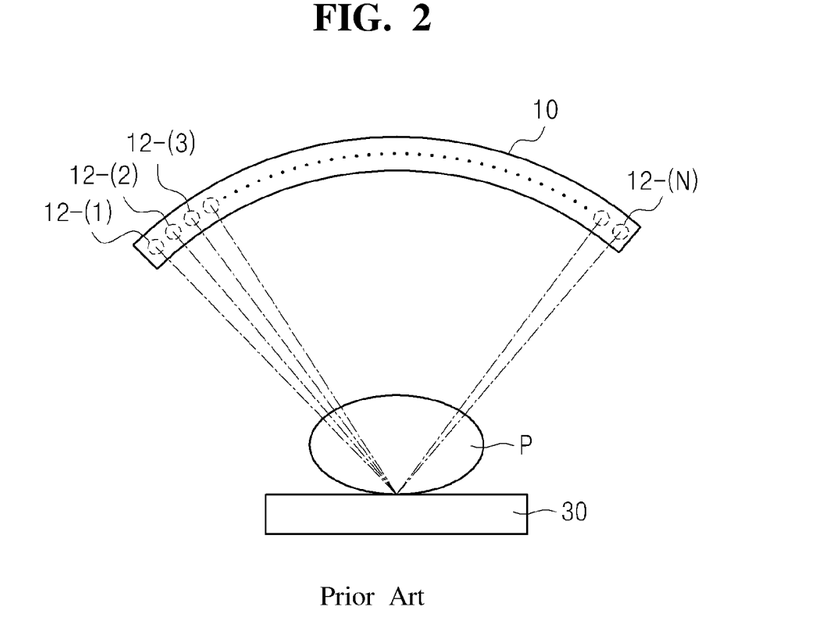
FIG. 2 is a view illustrating acquisition of a radiation image from a radiographic apparatus.

FIG. 1 is a view illustrating a digital breast tomosynthesis (DBT) device. FIG. 2 is a view illustrating acquisition of a radiation image from a radiographic apparatus.

Referring to FIGS. 1 and 2, a DBT device 1 includes: a support 40 having a lower end portion fixed to the bottom; a body 50 provided to be able to raise or lower along the support 40; a radiation detector 30 provided on a lower portion of the body 50; and a radiation irradiating unit 10 provided on an upper portion of the body 50.

The DBT device 1 allows the body 50 to be adjusted in height by being raised or lowered along the support 40 such that a subject's object P to be photographed (for example, breasts) is placed on the radiation detector 30 when the subject enters a photographing position and allows the radiation irradiating unit 10 to photograph the object P so as to acquire a radiation image.

Although not illustrated, a radiographic apparatus used in a conventional DBT device relatively rotates one radiation source with respect to an object to acquire a projection image. That is, the one radiation source is moved to each of an N number of positions, that is, 12-1, 12-2, . . . , 12-N, so as to acquire a projection image.

However, such the radiographic apparatus lowers image quality because movement of the radiation source causes a motion blur phenomenon that the boundary of an image acquired by a radiation detector appears unclear. Further, when the radiation source is completely stopped at a photographing angle and a projection image is captured while the radiation source is relatively rotated with respect to the object, a total photographing time is increased because photographing needs to be performed at each position while the radiation source comes to a complete stop.

To solve the problem, the radiographic apparatus may acquire projection images by means of a plurality of radiation sources 12 fixed with respect to the object P, as illustrated in FIG. 2. In this case, the radiation sources are provided as an N number of radiation sources and arranged to be fixed at the positions of 12-1, 12-2, . . . , 12-N for photographing angles so as to acquire the projection images at the respective positions.

In this case, the radiographic apparatus may prevent the motion blur phenomenon, but may increase product costs because of using the plurality of radiation sources 12 all arranged to be fixed at the positions for the photographing angles, thereby increasing maintenance costs. Further, when the plurality of radiation sources 12 are disposed, the arrangement interval is reduced, and thus, it is difficult for the radiation sources 12 to be provided in a desired arrangement.

As illustrated in FIGS. 3 to 6, a radiographic apparatus, in accordance with an exemplary embodiment, includes: a radiation irradiating unit 100 having a plurality of radiation sources 120 and configured to irradiate an object P with radiation emitted from each of the plurality of radiation sources 120; a driving unit 400 configured to move the radiation irradiating unit 100; and a radiation detector 300 configured to detect the radiation passing through the object P so as to acquire a plurality of radiation images.

Here, the radiation sources 120 are arranged in one direction, and the radiation irradiating unit 100 is moved by the driving unit 400 in a direction in which the radiation sources 120 are arranged to acquire the plurality of radiation images before and after the movement.

Figure 3:
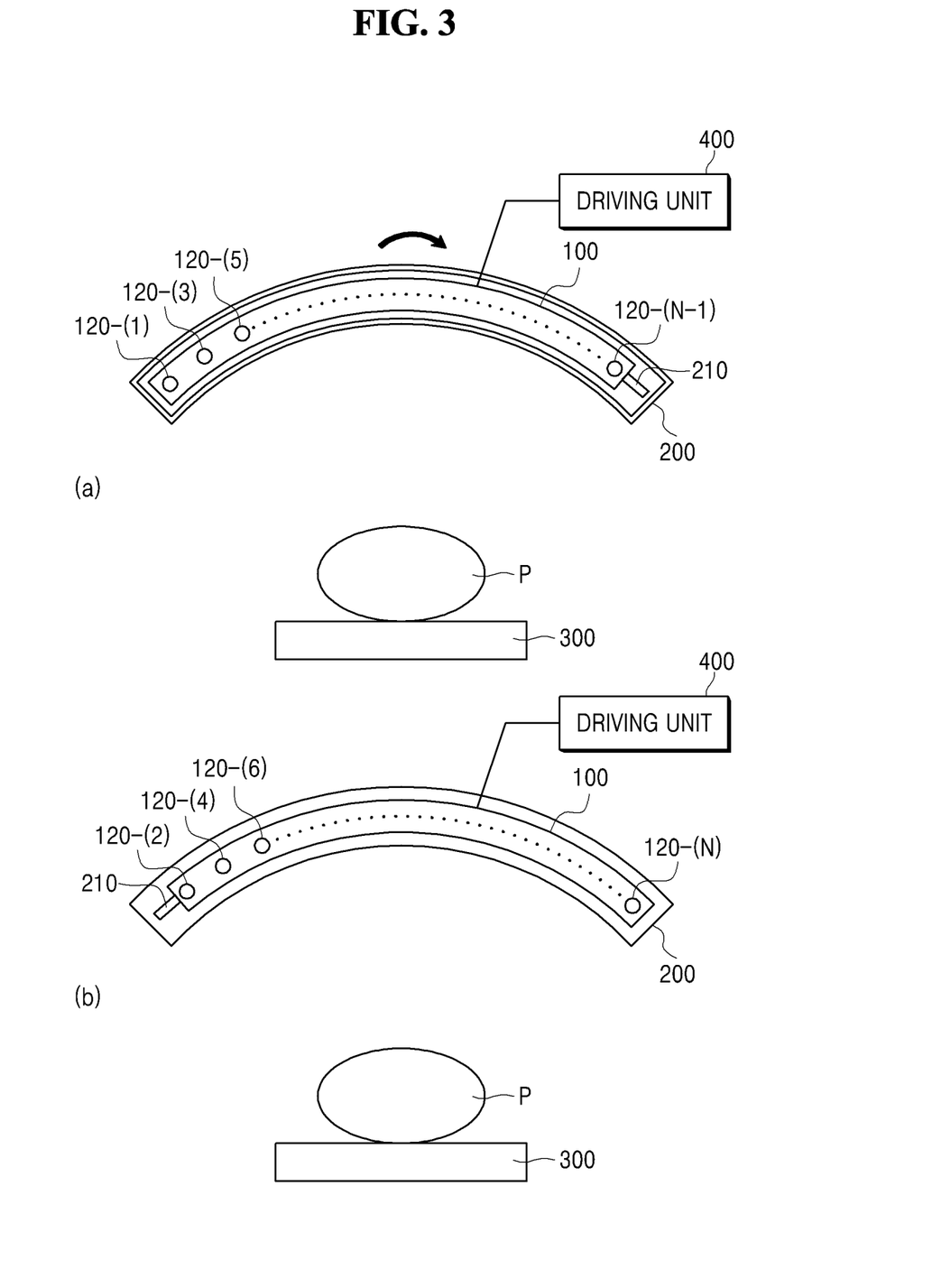
FIG. 3 is a view schematically illustrating a radiographic apparatus in accordance with an exemplary embodiment of the present disclosure.
Figure 4:
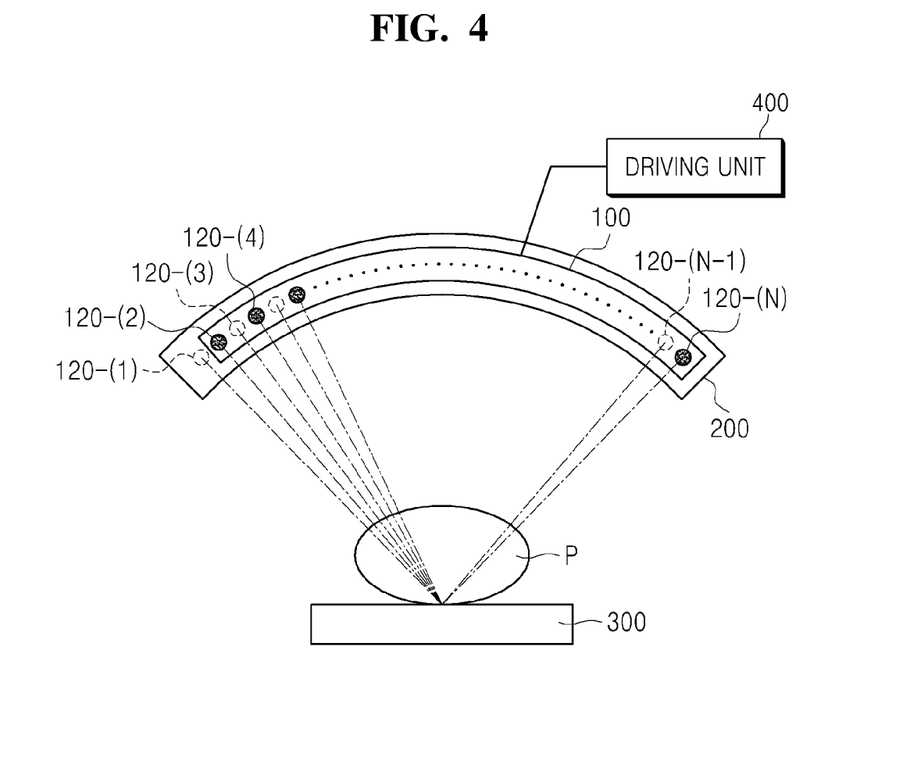
FIG. 4 is a view illustrating acquisition of a radiation image in accordance with an exemplary embodiment of the present disclosure.
Figure 5:
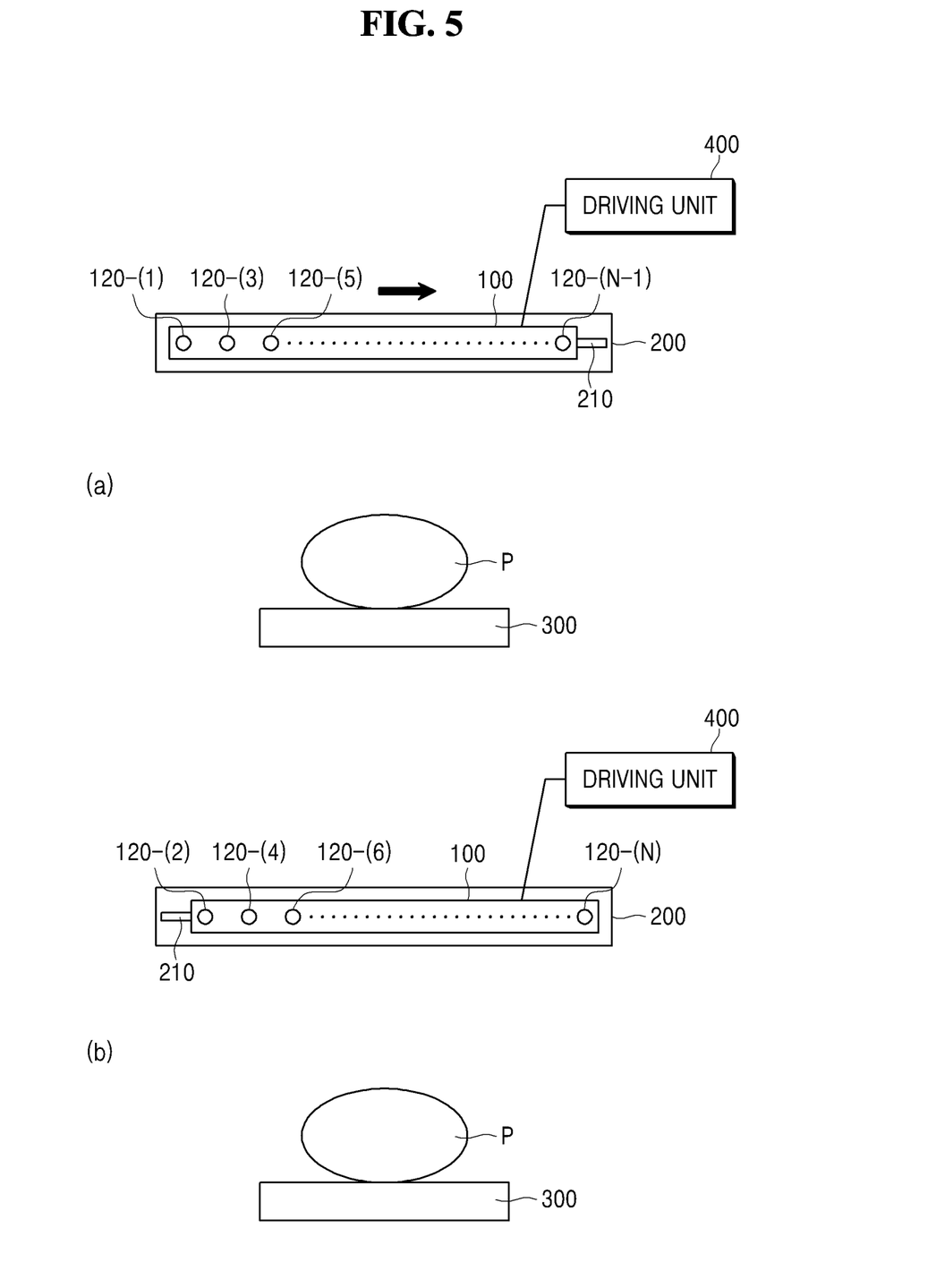
FIG. 5 is a view schematically illustrating a radiographic apparatus in accordance with another exemplary embodiment of the present disclosure.
Figure 6:
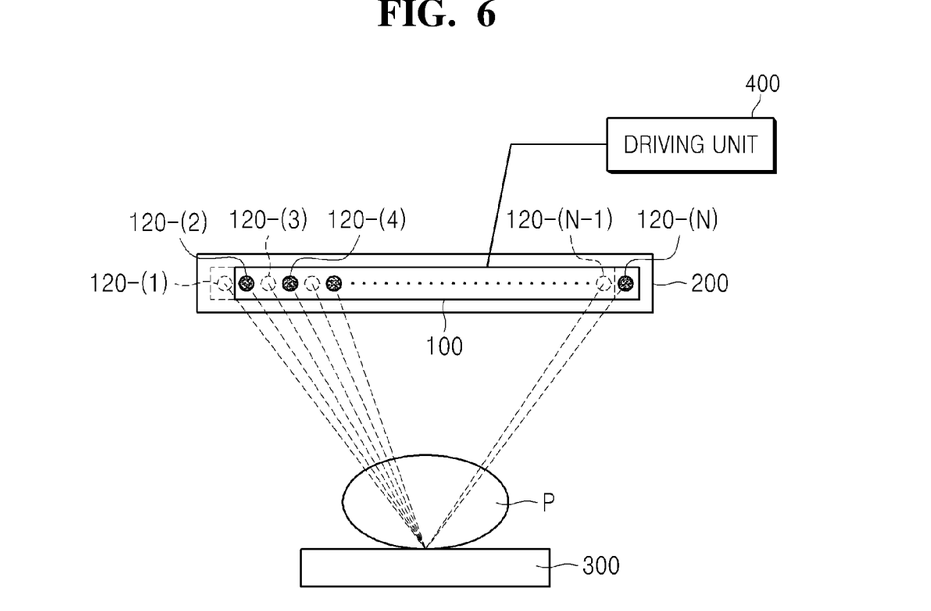
FIG. 6 is a view illustrating acquisition of a radiation image in accordance with another exemplary embodiment of the present disclosure.

Referring to FIGS. 3 and 4, an exemplary embodiment is described in which the direction of arrangement of the radiation sources 120 is arranged in an arc shape, and referring to FIGS. 5 and 6, another exemplary embodiment is described in which the direction of arrangement of the radiation sources 120 is arranged in a linear shape. However, the direction of arrangement of the radiation sources 120 is not limited thereto and may be applied to all cases in which the radiation sources 120 are arranged in one direction.

Further, in exemplary embodiments to be described below, radiation refers to electromagnetic waves including not only X rays but also α, β, and γ rays, and the object P irradiated with the radiation may be human breasts but is not limited thereto.

FIG. 3 is a view schematically illustrating a radiographic apparatus in accordance with an exemplary embodiment. FIG. 4 is a view illustrating acquisition of a radiation image in accordance with an exemplary embodiment.

Referring to FIGS. 3 and 4, the plurality of radiation sources 120 may be arranged in the arc shape in the radiographic apparatus in accordance with an exemplary embodiment.

The radiation sources 120 emit the radiation. To this end, the radiation source 120 may generate the radiation by irradiating a target with an electron beam and may include a field emission electrode configured to generate electrons in an emitter electrode by applying an electric field thereto. Here, the field emission electrode may be configured such that electrons are easily emitted even when applying a small electric field by using the field emission electrode including a protruding tip portion, and carbon nanotubes, having a very high field enhancement factor due to having a geometric structure with a low work function and a high aspect ratio, may be used as the tip portion of the field emission electrode.

Further, the radiation source 120 may also include a thermionic emission electrode configured to generate electrons by heating a filament. In this case, thermal electrons are generated while the filament is heated by power applied to the filament, and the generated thermal electrons generate radiation by colliding with the target.

The radiation source 120 is provided on the radiation irradiating unit 100 as the plurality of radiation sources to each emit the radiation. Each of the radiation sources 12 emits the radiation towards an irradiating position, for example, a central portion of the radiation detector 300, and the object P positioned on the radiation detector 300, for example, breasts, is irradiated with the radiation emitted from the radiation source 120.

The radiation source 120, in accordance with an exemplary embodiment, is provided as the plurality of radiation sources, but provided as a number of radiation sources less than the number of projection images required to synthesize a three-dimensional image. When radiation projection images acquired at an N number of positions, for example, 16 positions for photographing angles are required to synthesize a three-dimensional image, the radiation source 120, in accordance with an exemplary embodiment, may be provided as an NA number of radiation sources, for example, four or eight. Thus, an installation space of the radiation source 120 may be obtained, product costs may be reduced, and maintenance and repair may be facilitated by reducing the number of the radiation sources 120 to be smaller than the number of radiation projection images required to synthesize the three-dimensional image.

The radiation sources 120 may be provided to be arranged on the radiation irradiating unit 100 in the arc shape, as illustrated in FIGS. 3 and 4. When the radiation sources 120 are arranged in the arc shape, the distances between the radiation sources 120 and the radiation detector 300 in the direction of irradiation of the radiation sources 120, for example, the intervals between the central portion of the radiation detector 300 corresponding to a transmitting position, which is a position extending in the direction of irradiation of the radiation sources 120 and reaching the radiation detector 300, may be maintained to be the same with respect to the respective radiation sources 120. Thus, the radiation emitted from the respective radiation sources 120 may be incident on the object P at a uniform intensity. Here, the direction of irradiation refers to a direction along a centerline of the radiation emitted from the radiation source 120.

The radiation irradiating unit 100 has the plurality of radiation sources 120 provided thereon. As will be described below, the radiation irradiating unit 100 is moved by the driving unit 400 in the direction of arrangement of the radiation sources 120, that is, in the arc shape. In the drawings, the radiation irradiating unit 100 is illustrated as being formed in the same shape as the direction of arrangement of the radiation sources 120, that is, in the arc shape, but the radiation irradiating unit 100 has the plurality of radiation sources 120 and may be formed in various shapes capable of supporting the radiation sources 120.

The plurality of radiation sources 120 may be provided on the radiation irradiating unit 100 at the same intervals. Since the respective radiation sources 120 are provided on the radiation irradiating unit 100 at the same intervals, the differences in the positions of the respective radiation sources 120 before and after the radiation sources 120 are moved according to the movement of the radiation irradiating unit 100 may be maintained to be the same. Thus, radiation projection images are acquired at the respective positions disposed at predetermined intervals.

Further, the intervals between the plurality of radiation sources 120 are maintained according to the movement of the radiation irradiating unit 100 to move in conjunction with the radiation irradiating unit 100. That is, the plurality of radiation sources 120 are provided on the radiation irradiating unit 100 at the same intervals, and, as the radiation irradiating unit 100 is moved by the driving unit, the plurality of radiation sources 120 integrally move with the same intervals therebetween. A process of acquiring a radiation projection image while the radiation sources 120 move integrally with the radiation irradiating unit 100 will be described later in connection with a process of operating the driving unit.

The driving unit 400 moves the radiation irradiating unit 100 in the direction in which the radiation sources 120 are arranged. As illustrated in FIGS. 3 and 4, when the plurality of radiation sources 120 are arranged in the arc shape, the driving unit 400 moves the radiation irradiating unit 100 in the arc shape. The driving unit 400 may move the radiation irradiating unit 100 by using a motor or an electromagnet. To easily control a direction of movement of the radiation irradiating unit 100, the radiographic apparatus in accordance with an exemplary embodiment further includes a supporting unit 200 on which the radiation irradiating unit 100 is seated, and the driving unit 400 may move the radiation irradiating unit 100 on the supporting unit 200. In this case, the supporting unit 200 may have a guide 210 extending along a moving path of the radiation irradiating unit 100, and the radiation irradiating unit 100 may be coupled to the guide 210 formed on the supporting unit 200 to move along the guide 210. Such a guide may be formed as a linear motion (LM) guide or a rail capable of moving the radiation irradiating unit 100 along the moving path, and a bearing or the like may be provided along the guide 210 to reduce the resistance to the radiation irradiating unit 100 coupled to the guide 210.

Hereinafter, a case in which the radiation projection images acquired at the N number of positions for the photographing angles are required to synthesize the three-dimensional image will be described as an example with respect to the process of operating the driving unit.

(a) of FIG. 3 is a view schematically illustrating the radiographic apparatus in accordance with an exemplary embodiment before the movement of the radiation irradiating unit 100. (b) of FIG. 3 is a view schematically illustrating the radiographic apparatus in accordance with an exemplary embodiment after the movement of the radiation irradiating unit 100.

When the N number of images are required to synthesize the three-dimensional image, the plurality of radiation sources 120 may be provided as the NA number of radiation sources less than the number of the projection images required to synthesize the three-dimensional image, as described above.

Referring to (a) of FIG. 3, the respective radiation sources 120 before the movement may be provided to respectively correspond to the positions of 120-(1), 120-(3), 120(5), ..., 120-(N−1) when provided as the NA number of radiation sources (in this case, NA=N/2). Further, although not illustrated, the plurality of radiation sources 120 may also be provided to respectively correspond to the positions of 120-(1), 120-(2), 120(3), ..., 120-(N/2). Here, that is, the number NA of the plurality of radiation sources 120 may be a value obtained by dividing the number N of the projection images required to synthesize the three-dimensional image by an integer greater than 1 and less than N.

The plurality of radiation sources 120 are provided on the radiation irradiating unit 100 and moved by the driving unit 400 in the direction in which the radiation sources 120 are arranged. In this case, the supporting unit 200 on which the radiation irradiating unit 100 is seated is further included to easily control the direction in which the radiation irradiating unit 100 moves, and the driving unit 400 may move the radiation irradiating unit 100 on the supporting unit 200, as described above.

Referring to (b) of FIG. 3, the respective radiation sources 120 after the movement may be respectively arranged at the positions, that is, 120-(2), 120-(4), 120(6), ..., 120-(N), at which the respective radiation sources 120 after the movement and those before the movement do not overlap each other. In this case, the driving unit 400 moves the radiation irradiating unit 100 having the respective radiation sources 120 by a distance shorter than the interval between the respective radiation sources 120. Thus, a moving time of the radiation irradiating unit 100 may be shortened, thereby reducing a total photographing time for acquisition of the radiation projection images required to synthesize the three-dimensional image. Further, when the plurality of radiation sources 120 before the movement are provided to be respectively arranged at the positions of 120-(1), 120-(2), 120(3), ..., 120-(N/2), the respective radiation sources 120 after the movement may be respectively arranged at the positions of 120-(N/2+1), 120-(N/2+2), 120(N/2+3), ..., 120-(N).

For example, when the radiation projection images acquired at the 16 positions of 120-(1), 120-(2), 120-(3), ..., 120-(16) are required to synthesize the three-dimensional image, the radiation sources 120 may be provided at the positions of 120-(1), 120-(3), 120-(5), ..., 120-(15) so as to respectively capture a plurality of first radiation images and may be moved by the driving unit 400 to the positions of 120-(2), 120-(4), 120-(6), ..., 120-(16) so as to respectively capture a plurality of second radiation images. Further, the radiation sources 120 may be provided at the positions of 120-(1), 120-(2), 120-(3), ..., 120-(8) before the movement so as to respectively capture the plurality of first radiation images and may be moved by the driving unit 400 to the positions of 120-(9), 120-(10), 120-(11), ..., 120-(16) so as to respectively capture the plurality of second radiation images.

Here, the plurality of first radiation images and the plurality of second radiation images may be captured by activating the plurality of radiation sources 120 in sequential or random order. That is, the order of activation of the respective radiation sources 120 is not particularly limited when the radiation images required to synthesize the three-dimensional image are all acquired by means of the first radiation images and the second radiation images.

In the above, a case in which the number NA of the plurality of radiation sources 120 is half of the number N of the projection images required to synthesize the three-dimensional image has been described as an example. However, projection images required to synthesize an entire three-dimensional image may be captured by setting the number NA of the plurality of radiation sources 120 to be ⅓ or ¼ of the number N of the projection images required to synthesize the three-dimensional image and moving the radiation irradiating unit 100 step by step by means of the driving unit. That is, the relationship between the number NA of the plurality of radiation sources 120 and the number N of the projection images required to synthesize the three-dimensional image may be expressed as an equation of NA=N/n (where n is an integer greater than 1 and less than N)). In this case, a moving distance L of the radiation irradiating unit 100 obtained by means of the driving unit 400 may be expressed as an equation of L=D/n with respect to an interval D between the respective radiation sources 120, and the number of times M of stepwise movements of the radiation irradiating unit 100 may be expressed as (n−1) times.

Further, an exemplary embodiment as an example has been described in which projection images are captured from all of the radiation sources 120 at a first position before the movement of the radiation irradiating unit 100 and projection images are captured from all of the radiation sources 120 at a second position after the movement of the radiation irradiating unit 100. However, various methods for capturing projection images at respective positions may also be applied, including capturing projection images from a portion of the radiation sources 120 through movement thereof in a direction from the first position to the second position and then capturing projection images from the remainder of the radiation sources 120 through movement thereof in a direction from the second position to the first position.

The radiation detector 300 detects the radiation passing through the object P so as to acquire the plurality of radiation images. The radiation detector 300 may include a digital radiation detector 300 using a thin film transistor and detects the radiation emitted from each of the plurality of radiation sources 120 before the movement and passing through the object P and detects the radiation emitted from each of the plurality of radiation sources 120 after the movement and passing through the object P so as to acquire the plurality of first radiation images and the plurality of second radiation images.

As described above, the radiographic apparatus in accordance with an exemplary embodiment may prevent a motion blur phenomenon due to movement of the radiation sources 120 by capturing an image in a state in which a number of radiation sources 120 less than the number of the radiation projection images required to synthesize the three-dimensional image are fixed, and may reduce a photographing time for acquisition of the entire radiation projection images may be reduced by minimizing the moving distance of the radiation irradiating unit 100.

Furthermore, the radiation projection images of the object P may be quickly captured at various angles through the plurality of radiation sources 120 arranged in a predetermined direction to acquire a high-resolution three-dimensional image, thereby enabling an accurate diagnosis of a lesion for the object P.

FIG. 5 is a view schematically illustrating a radiographic apparatus in accordance with another exemplary embodiment. FIG. 6 is a view illustrating acquisition of a radiation image in accordance with another exemplary embodiment.

The radiographic apparatus of FIGS. 5 and 6 in accordance with another exemplary embodiment differs from the radiographic apparatus of FIGS. 3 and 4 in accordance with the exemplary embodiments only in the direction in which the radiation sources 120 are arranged. Thus, a description overlapping with the above-mentioned description with respect to the radiographic apparatus in accordance with an exemplary embodiment will be omitted.

The radiation sources 120 may be provided to be arranged on a radiation irradiating unit 100 in a linear shape. (a) of FIG. 5 is a view schematically illustrating the radiographic apparatus in accordance with another exemplary embodiment before the movement of the radiation irradiating unit 100. (b) of FIG. 5 is a view schematically illustrating the radiographic apparatus in accordance with another exemplary embodiment after the movement of the radiation irradiating unit 100.

Referring to (a) of FIG. 5, the respective radiation sources 120 before the movement may be provided to respectively correspond to the positions of 120-(1), 120-(3), 120(5), . . . , 120-(N−1) when provided as an NA number of radiation sources (in this case, NA=N/2). Further, although not illustrated, the plurality of radiation sources 120 may also be provided to respectively correspond to the positions of 120-(1), 120-(2), 120(3), . . . , 120-(N/2). Here, that is, the number NA of the plurality of radiation sources 120 may be a value obtained by dividing the number N of projection images required to synthesize a three-dimensional image by an integer greater than 1 and less than N.

Referring to (b) of FIG. 5, the respective radiation sources 120 after the movement may be respectively arranged at the positions, that is, 120-(2), 120-(4), 120(6), . . . , 120-(N), at which the respective radiation sources 120 after the movement and those before the movement do not overlap each other. In this case, the driving unit 400 moves the radiation irradiating unit 100 having the respective radiation sources 120 by a distance shorter than the intervals between the respective radiation sources 120. Thus, a moving time of the radiation irradiating unit 100 may be shortened, thereby reducing a total photographing time for acquisition of radiation projection images required to synthesize the three-dimensional image. Further, when the plurality of radiation sources 120 before the movement are provided to be respectively arranged at the positions of 120-(1), 120-(2), 120(3), . . . , 120-(N/2), the respective radiation sources 120 after the movement may be respectively arranged at the positions of 120-(N/2+1), 120-(N/2+2), 120(N/2+3), . . . , 120-(N).

Here, when the plurality of radiation sources 120 are arranged in an arc shape with a transmitting position as a center, the distances between the radiation sources 120 and a radiation detector 300 according to a direction of irradiation of the radiation sources 120 before and after the movement of the radiation irradiating unit 100 is maintained to be the same. However, when the plurality of radiation sources 120 are arranged in a linear shape, the transmitting position of the radiation sources 120 is changed according to the movement of the radiation irradiating unit 100. When the transmitting position is changed, the radiographic apparatus in accordance with another exemplary embodiment may maintain the transmitting positions before and after the movement of the radiation irradiating unit 100 to be the same by further including a controller (not illustrated) configured to control the direction of irradiation of the respective radiation sources 120 according to the movement of an irradiation part for radiation.

The controller controls the direction of irradiation of the respective radiation sources 120 such that the direction of irradiation faces the same position before and after the movement of the radiation irradiating unit 100. That is, as illustrated in (a) of FIG. 4, the plurality of radiation sources 120 before the movement are respectively arranged at the position of 120-(1), 120-(3), 120(5), . . . , 120-(N−1) so as to irradiate the radiation at the transmitting position, that is, in the direction of irradiation towards a central portion of the radiation detector 300. At this time, when the radiation irradiating unit 100 moves, the plurality of radiation sources 120 after the movement are respectively arranged at the positions of 120-(2), 120-(4), 120(6), . . . , 120-(N), and the transmitting position of the respective radiation sources 120 is changed by a moving distance of the radiation irradiating unit 100. Thus, the controller controls the direction of irradiation by rotating the respective radiation sources 120 or changing the locations of focuses within the radiation sources 120 such that the direction of irradiation of the radiation sources 120 after the movement corresponds to the direction of irradiation of the radiation sources 120 before the movement.

Further, when the radiation sources 120 are arranged in the linear shape, the control according to the intervals between the radiation sources 120 and the movement of the radiation irradiating unit 100 is facilitated. However, the intervals between the transmitting position for example, the central portion of the radiation detector 300 and the radiation sources 120, is different at the positions of the respective radiation sources 120.

When the radiation sources 120 are arranged in the linear shape so that the intervals between the central portion of the radiation detector 300 and the radiation sources 120 are different, the radiation emitted from at least two of the radiation sources 120 may be incident on an object P at different intensities. In this case, the difference in radiation intensities may be corrected by processing the radiation projection images obtained by the radiation incident at the different intensities. However, an additional image processing process may be omitted by controlling the intervals before the acquisition of the projection images.

Thus, the controller may control an amount of radiation emitted from the radiation sources 120 according to the intervals between the radiation sources 120 and the transmitting position such that the radiation emitted from the respective radiation sources 120 is incident on the object P at a uniform intensity. That is, the control may be performed such that the radiation emitted from the respective radiation sources 120 is incident on the object P at the uniform intensity by increasing the amount of radiation emitted from the radiation sources 120 when the intervals between the radiation sources 120 and the transmitting position are relatively great and decreasing the amount of radiation emitted from the radiation sources 120 when the intervals between the radiation sources 120 and the transmitting position are relatively less.

Figure 7:
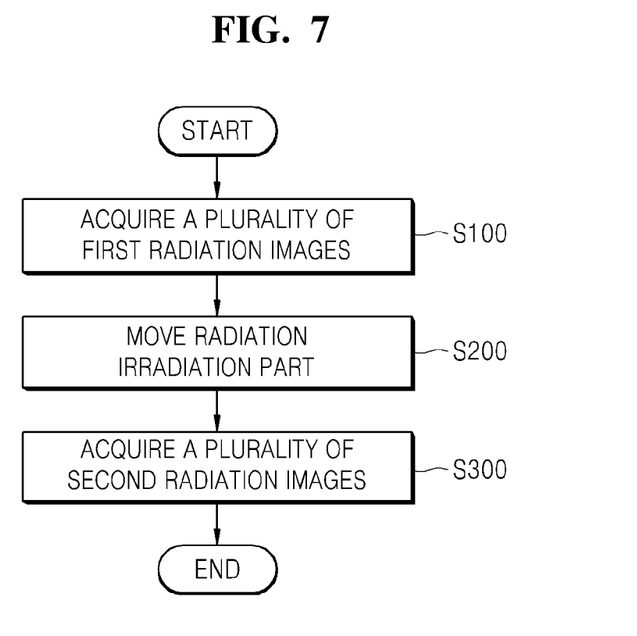
FIG. 7 is a view schematically illustrating a radiographic method in accordance with an exemplary embodiment of the present disclosure.

FIG. 7 is a view schematically illustrating a radiographic method in accordance with an exemplary embodiment.

Referring to FIG. 7, the radiographic method in accordance with an exemplary embodiment includes: acquiring a plurality of first radiation images by irradiating an object P with radiation emitted from a radiation irradiating unit 100 having a plurality of radiation sources 120 (S100); moving the radiation irradiating unit 100 in a direction in which the radiation sources 120 are arranged (S200); and acquiring a plurality of second radiation images by irradiating the object P with radiation emitted from the radiation irradiating unit 100 (S300).

The acquiring of the plurality of first radiation images (S100) includes acquiring the plurality of first radiation images by irradiating the object P with the radiation emitted from each of the plurality of radiation sources 120 before the movement of the radiation irradiating unit 100. At this time, the first radiation images may be acquired by activating the respective radiation sources 120 in sequential or random order.

That is, the respective radiation sources 120 may be provided to respectively correspond to the positions of 120-(1), 120-(3), 120(5), . . . , 120-(N−1) before the movement of the radiation irradiating unit 100. The radiation sources 120 provided at the respective positions are activated in the sequential or random order so as to irradiate the radiation, and the radiation emitted from the radiation sources 120 and passing through the object P is detected by the radiation detector 300 so as to acquire the plurality of first radiation images at the respective positions.

Here, when the plurality of radiation sources 120 are arranged in a linear shape, the intervals between a transmitting position and the radiation sources 120 at the respective positions of the radiation sources 120 are different. In this case, the radiation emitted from at least two of the radiation sources is incident at different intensities to acquire the first radiation images, and the difference in radiation intensities may be corrected by processing the first radiation images. However, the amount of radiation emitted from the radiation sources 120 may also be controlled such that the radiation is incident on the object P at a uniform intensity in the image acquisition process.

Thus, the acquiring of the first radiation images includes acquiring the plurality of first radiation images by adjusting the amount of radiation emitted from the radiation sources 120 such that the radiation emitted from the respective radiation sources 120 is incident on the object P at the uniform intensity, that is, such that the amount of radiation emitted from the radiation sources 120 is increased when the intervals between the radiation sources 120 and the transmitting position are relatively great and such that the amount of radiation emitted from the radiation sources 120 is decreased when the intervals between the radiation sources 120 and the transmitting position are relatively less, as described above.

The moving of the radiation irradiating unit 100 in the direction of arrangement of the radiation sources 120 (S200) includes moving the radiation irradiating unit 100 along an arc when the radiation sources 120 are arranged in an arc shape and moving the radiation irradiating unit 100 along a linear line when the radiation sources 120 are arranged in the linear shape.

Here, a driving unit 400 may move the radiation irradiating unit 100 by using a motor or an electromagnet, a supporting unit 200 on which the radiation irradiating unit 100 is seated is further included in the radiographic apparatus in accordance with an exemplary embodiment, and a direction of movement of the radiation irradiating unit 100 may be easily controlled by moving the radiation irradiating unit 100 on the supporting unit 200, as described above. Further, when moving the radiation irradiating unit 100 in the direction of arrangement of the radiation sources 120, the driving unit 400 moves the radiation irradiating unit 100 such that the radiation sources 120 are arranged at positions at which the radiation sources 120 do not overlap each other before and after the movement of the radiation irradiating unit 100. In this case, the driving unit 400 moves the radiation irradiating unit 100 by a distance shorter than the intervals between the radiation sources 120. Thus, a moving time of the radiation irradiating unit 100 may be shortened, and a total photographing time for acquisition of radiation projection images required to synthesize a three-dimensional image may be reduced, as described above. The respective radiation sources 120 are respectively arranged at the positions of 120-(2), 120-(4), 120(6), . . . , 120-(N) after the movement of the radiation irradiating unit 100. The acquiring of the plurality of second radiation images (S300) includes acquiring the plurality of second radiation images by irradiating the object P with the radiation emitted from each of the plurality of radiation sources 120 after the movement of the radiation irradiating unit 100. At this time, the first radiation images may be acquired by activating the respective radiation sources 120 in sequential or random order.

That is, the respective radiation sources 120 may be arranged to respectively correspond to the positions of 120-(2), 120-(4), 120(6), . . . , 120-(N) after the movement of the radiation irradiating unit 100. The radiation sources 120 arranged at the respective positions are activated in the sequential or random order so as to irradiate the radiation, and the radiation emitted from the radiation sources 120 and passing through the object P is detected by the radiation detector 300 so as to acquire the plurality of second radiation images at the respective positions.

Further, when the plurality of radiation sources 120 are arranged in the linear shape, the intervals between the transmitting position and the radiation sources 120 at the respective positions of the radiation sources 120 are different. Thus, the acquiring of the second radiation images includes acquiring the plurality of second radiation images by adjusting the amount of radiation emitted from the radiation sources 120 such that the radiation emitted from the respective radiation sources 120 is incident on the object P at the uniform intensity, that is, such that the amount of radiation emitted from the radiation sources 120 is increased when the intervals between the radiation sources 120 and the transmitting position are relatively great and such that the amount of radiation emitted from the radiation sources 120 is decreased when the intervals between the radiation sources 120 and the transmitting position are relatively less, as in the acquiring of the first radiation images. Further, the radiation emitted from at least two of the radiation sources is incident at different intensities to acquire the second radiation images, and the difference in radiation intensities may be corrected by processing the second radiation images, as described above.

Furthermore, when the plurality of radiation sources 120 are arranged in the linear shape, the transmitting position of the radiation sources 120 may be changed according to the movement of the radiation irradiating unit 100. Thus, the radiographic method in accordance with an exemplary embodiment may further include changing the direction of irradiation of the respective radiation sources 120 such that the direction of irradiation of the radiation sources 120 faces the same transmitting position as that before the movement of the radiation sources 120.

The changing of the direction of irradiation of the respective radiation sources 120 includes changing the direction of irradiation by rotating the respective radiation sources 120 or changing the locations of focuses within the radiation sources 120 such that the direction of irradiation of the radiation sources 120 after the movement corresponds to the direction of irradiation of the radiation sources 120 before the movement. Such a process may prevent an additional time from being required according to a change in the direction of irradiation of the radiation sources 120 by being simultaneously performed with the moving of the radiation irradiating unit 100 in the direction in which the radiation sources 120 are arranged.

The radiation images required to synthesize the three-dimensional image may be all obtained by means of the first radiation images and the second radiation images acquired in the above-mentioned processes. The obtained first and second radiation images at the N number of positions for the photographing angles are synthesized by reconstruction processing to generate a plurality of tomographic images. Reconstruction processing may be performed by using a filtered back projection (FBP) method. In such calculation processing, a measured radiation projection image is reversely projected by filtering. The plurality of tomographic images generated by reconstruction processing may be displayed as three-dimensional images corresponding to planes of different distances.

In the above, although the exemplary embodiments of the present invention have been illustrated and described using specific terms, such terms are merely for the purpose of clarifying the invention. It would be obvious that various changes and modifications may be made to the embodiments and terms of the invention without departing from the spirit and scope of the following claims. Such modified embodiments should not be individually understood from the spirit and scope of the present invention but should be construed as being within the claims of the present invention.

The invention claimed is:

1. A radiographic apparatus comprising:
a radiation irradiating unit having a plurality of radiation sources having an interval between each radiation source and configured to irradiate an object with radiation emitted from each of the plurality of radiation sources;
a supporting unit on which the radiation irradiating unit is seated;
a driving unit configured to move the radiation irradiating unit on the supporting unit; and
a radiation detector configured to detect the radiation passing through the object to acquire a plurality of radiation images;
wherein the plurality of radiation sources are moved integrally with the radiation irradiating unit with the interval maintained,
wherein a number NA of the plurality of radiation sources has a value obtained by dividing a number N of the plurality of radiation images that are necessary for tomosynthesis by an integer n that is greater than 1 and less than N,
wherein the driving unit moves the radiation irradiating unit, in a stepwise manner, n−1 times by a distance of D/n, where D is the interval between each radiation source,
wherein the plurality of radiation sources irradiate the object with the radiation at various angles according to the movement of the radiation irradiating unit to acquire the plurality of radiation images that are necessary for tomosynthesis, and
wherein a guide is formed on the supporting unit, the guide extending along a moving path of the radiation irradiating unit,
wherein the radiation irradiating unit is coupled to the guide to move along the guide, and
wherein the plurality of radiation sources irradiate the radiation toward a same position on the radiation detector before and after the movement of the radiation irradiating unit.

2. The radiographic apparatus of claim 1, wherein the plurality of radiation sources are arranged in one direction, and the radiation irradiating unit moves in a direction in which the plurality of radiation sources are arranged.

3. The radiographic apparatus of claim 1, wherein the plurality of radiation sources are provided on the radiation irradiating unit at a same interval.

4. The radiographic apparatus of claim 1, wherein the driving unit moves the radiation irradiating unit such that the plurality of radiation sources are arranged at positions at which the radiation sources do not overlap each other before and after the movement of the radiation irradiating unit.

5. The radiographic apparatus of claim 1, further comprising a controller configured to control a direction of irradiation of each of the plurality of radiation sources according to the movement of the radiation irradiating unit.

6. The radiographic apparatus of claim 1, wherein an amount of emission of radiation from the plurality of radiation sources is controlled according to a distance between the radiation source and the radiation detector in a direction of irradiation of the radiation source.

7. The radiographic apparatus of claim 1, wherein the plurality of radiation sources include a field emission electrode configured to generate electrons by applying an electric field.

8. The radiographic apparatus of claim 1, wherein the plurality of radiation sources include a thermionic emission electrode configured to generate electrons by heating a filament.

9. The radiographic apparatus of claim 5, wherein the controller controls the direction of irradiation of each radiation source of the plurality of radiation sources such that the direction of irradiation faces a same position as that before and after the movement of the radiation irradiating unit.

10. A radiographic method comprising:
acquiring a plurality of first radiation images by irradiating an object with radiation emitted from a radiation irradiating unit having a plurality of radiation sources having an interval between each radiation source;
moving the radiation irradiating unit in a direction in which the radiation sources are arranged; and
acquiring a plurality of second radiation images by irradiating the object with radiation emitted from the radiation irradiating unit;
wherein a number NA of the plurality of radiation sources has a value obtained by dividing a total number N of the plurality of first radiation images and the plurality of second radiation images that are necessary for tomosynthesis by an integer n that is greater than 1 and less than N;
wherein the moving of the radiation irradiating unit comprises:
moving the plurality of radiation sources integrally with the radiation irradiating unit with the interval maintained;
moving the radiation irradiating unit, in a stepwise manner, n−1 times by a distance of D/n, where D is the interval between each radiation source; and
irradiating the object with the radiation at various angles by the plurality of radiation sources according to the movement of the radiation irradiating unit to acquire the plurality of first radiation images and the plurality of second radiation images that are necessary for tomosynthesis,
wherein the radiation irradiating unit is coupled to a guide and the guide is formed on a supporting unit and extends along a moving path of the radiation irradiating unit, wherein moving the radiation irradiating unit comprises moving the radiation irradiating unit along the guide, and
wherein the plurality of radiation sources irradiate the radiation toward a same position on a radiation detector before and after the movement of the radiation irradiating unit, the radiation detector being configured to detect the radiation passing through the object.

11. The radiographic method of claim 10, wherein the acquiring of the plurality of first radiation images and the acquiring of the plurality of second radiation images include respectively acquiring the plurality of first radiation images and the plurality of second radiation images by sequentially activating the plurality of radiation sources.

12. The radiographic method of claim 10, wherein the acquiring of the plurality of first radiation images and the acquiring of the plurality of second radiation images include respectively acquiring the plurality of first radiation images and the plurality of second radiation images by activating the plurality of radiation sources in random order.

13. The radiographic method of claim 10, wherein the acquiring of the plurality of first radiation images and the acquiring of the plurality of second radiation images include respectively acquiring the plurality of first radiation images and the plurality of second radiation images by allowing radiation emitted from at least two of the plurality of radiation sources to be incident on the object at different intensities.

14. The radiographic method of claim 10, wherein the acquiring of the plurality of first radiation images and the acquiring of the plurality of second radiation images include respectively acquiring the plurality of first radiation images and the plurality of second radiation images by adjusting an amount of emission of radiation emitted from each radiation source of the plurality of radiation sources such that the radiation is incident on the object at a uniform intensity.

15. The radiographic method of claim 10, further comprising changing a direction of irradiation of each of the plurality of radiation sources such that the direction of irradiation faces a same position as that before the moving of the radiation irradiating unit.

16. The radiographic method of claim 15, wherein the changing of the direction of irradiation of the plurality of radiation sources is performed simultaneously with the moving of the radiation irradiating unit.

* * * * *